United States Patent
Kolta

[11] Patent Number: 6,139,876
[45] Date of Patent: Oct. 31, 2000

[54] GEL WITH INCREASED OXYGEN CONTENT

[75] Inventor: Péter Kolta, Pécs, Hungary

[73] Assignees: Jozsef Ladanyi; a part interest; Mihaly Lantos, both of Budapest, Hungary; a part interest

[21] Appl. No.: 08/958,467

[22] Filed: Oct. 27, 1997

Related U.S. Application Data

[63] Continuation of application No. PCT/HU96/00022, Apr. 26, 1996.

[30] Foreign Application Priority Data

Apr. 26, 1995 [HU] Hungary .................................. 9501193

[51] Int. Cl.$^7$ ...................................................... A61K 9/00
[52] U.S. Cl. ........................... 424/484; 424/43; 424/400; 424/401; 424/405; 424/485; 424/486; 424/659; 544/25; 544/42; 544/944
[58] Field of Search ...................................... 424/400, 401, 424/405, 43, 659, 446, 484–486; 514/25, 42, 944

[56] References Cited

U.S. PATENT DOCUMENTS

| | | | |
|---|---|---|---|
| 3,011,950 | 12/1961 | Mehaffey | 514/944 |
| 3,445,563 | 5/1969 | Clegg et al. | 514/944 |
| 3,639,575 | 2/1972 | Schmolka et al. | 514/557 |
| 5,152,757 | 10/1992 | Ericksson | 604/305 |
| 5,587,175 | 12/1996 | Viegar et al. | 424/427 |
| 5,658,956 | 8/1997 | Martin et al. | 514/724 |

*Primary Examiner*—Neil S. Levy
*Attorney, Agent, or Firm*—Finnegan, Henderson, Farabow, Garrett & Dunner, L.L.P.

[57] ABSTRACT

A gelatin with increased oxygen content for pharmaceutical, cosmetic and/or veterinary use. The gelatin comprises a gelling agent and a solvent, furthermore oxygen in a substantially even distribution with a pressure exceeding normal atmospheric pressure, wherein the surface tension of the gelatin is sufficiently high to retain at least a portion of the overpressure of the oxygen throughout a predetermined period of time after having been exposed ton atmospheric environment. Glucose and bactericide and/or fungicide agents can be added to facilitate cellular metabolism and decrease the danger of local infections. The solvent can be distilled water or a physiologic saline solution.

18 Claims, 22 Drawing Sheets

GEL WITH INCREASED OXYGEN CONTENT

This application is a Continuation of International Application PCT/HU96/00022, with an International filing date of Apr. 26, 1996.

The invention relates to a gel with increased oxygen content for pharmaceutical cosmetic and/or veterinary use, and a method for preparing the gel.

It has been known for a long time that ossein-products like gelatin alba are excellent base materials for different kinds of pharmaceuticals. In room temperature the water based solution of such materials forms a gel if the concentration exceeds about 1–1.5%. It is also known that gels, especially gelatin can be used for treating different kinds of skin wounds, e.g. burns or frost wounds. The gel is applied under a cover primarily for treating combustio erythematosa. It is also well-known in the art that gels, particularly gelatin are ideal media for bacterial cultures, and in the treatment of burn or frost wounds there is a dilemma whether gelatin can be used at all and whether such use should take place under a cover or not. The primary problem connected with a covered treatment lies in the potential danger of the proliferation of anaerobe bacteria.

Probably it has been due to the increased danger of infection that gelatin, which comprises the basic components of the cells i.e. proline and hydroxi-proline as well as glycine and other amino acids and which has excellent penetration properties into the skin, has not been used widely in the field of cosmetics and pharmaceuticals.

The healing mechanism of different kinds of wounds, particularly of skin wounds is more or less known. The regeneration of the destroyed area starts from the edges of the wounds and the materials required for the regeneration process are transported by the blood flowing through the newly formed capillaries. This is the reason why the healing process starts from the edge regions and the central areas heal later. No mechanism has been known which could result in the spatially uniform healing of the injured areas.

The German publication DE 42 36 607 A1 refers to a dermatological preparation which comprises a fluorocarbonic emulsion. The emulsion is enriched in oxygen, however, the partial pressure of oxygen is below the atmospheric one. The preparation utilizes the combined effect of oxygen and the flurocarbonic emulsion.

The object of the invention is to provide a gel which can promote the healing mechanism of wounds and other skin injuries by facilitating the function of cells so that the healing process will be more even than in case of natural regeneration.

A further object is to eliminate the reasons which have prevented so far the wide-scale application of gels in which anaerobe bacteria can proliferate.

According to the invention it has been recognized that certain gels, preferably gelatin can be saturated by oxygen applied with an overpressure compared to normal atmospheric one. It is preferable if oxygen is added when the gelatin component is already in a liquid phase (i.e. heated above the melting temperature) and being stirred. Gelling will take place when the material is cooled down to room temperature, and owing to the high surface tension and low gas permeability of the material oxygen will be embedded in the gel in the form of microscopically small bubbles. The so obtained material will have an opaque appearance due to the refraction of light at the boundaries of the tiny bubbles. Following exposure to the free atmosphere, the oxygen content of the gel will decrease gradually and the concentration exceeding normal equilibrium will be retained through a time period which is longer than the time required for the gel to be absorbed in the skin or living tissues.

It is preferable if the pressure of oxygen in the gel lies between 0.15 and 0.6 MPa and preferably between 0.3 and 0.55 MPa.

The oxygen transport to deeper layers is facilitated if the gelling agent, from which the gel has been made, has components that can be absorbed by living tissues, and metabolism is further facilitated if the gelling agent can be utilized by eucariotic cells.

Gelatin is considered to be the most preferable gelling agent. A preferable concentration range of gelatin is between about 1–3 mass %.

Gelatin and the oxygen encapsulated therein will have special synergetic effects. The intensive presence of oxygen will prevent proliferation of anaerobe bacteria which otherwise would rapidly multiply in the gelatin. The possibility of infection by aerobe bacteria or fungi cannot be excluded, however, there are several Gram positive and Gram negative antibiotics available which provide effective protection against such infections.

It can be supposed that the simultaneous presence of gelatin and oxygen promotes cellular metabolism, since in addition to oxygen required for metabolism, hydroxy-proline is also present that forms the major component of most desmosomes and skin cells.

To verify these hypothetical effects experiments have been designed that possess a sufficient selectivity so that not only the existence of the expected effects can be determined thereby, but also whether such effects can be attributed to the respective components alone or to their combined application.

The experiments confirmed the synergetic effect of gelatin and oxygen encapsulated therein, and the results were mainly due to the increased metabolism in the treated areas. When burn wounds were treated, the healing process did not start from the intact edge regions to proceed towards the central regions but an intensive healing was experienced at the whole wound area (i.e. also in the central regions). This was demonstrated both by the visual observation of the wound areas and by the results of histologic examinations.

In the following experiments the amount of the components will be given in mass percent units calculated relative to the full mass of the gel.

For excluding infections it is preferable if the gel comprises bactericide and/or fungicide agents. It is preferable if the agent is a non-oxidizing antibiotic applied in a therapeutically effective concentration. Such a preferable antibiotic is e.g. gentamicin sulfate present in an amount of 0.01 to 0.03 thousandth relative to the full gel mass.

Gentamicin sulfate can be used in case of open wounds as well. Mainly in case of external applications boric acid can be used in a therapeutical concentration of about 2.5 mass percent. Boric acid has an additional fungicidal effect as well.

Metabolism is substantially facilitated if glucose is also contained in the gel with a concentration required for the metabolism of the oxygen component supplied. This concentration is not identical in human and veterinary applications. In connection with the description of the experiments an example will be given to the concentration of glucose when guinea pigs are treated. This concentration proved to be not too critical, and according to the experiments the supplied glucose was consumed during the metabolism.

A preferable concentration range for glucose is between 10 and 50 mM/l, preferably between 30–40 mM/l.

If the gel is used to treating wounds wherein substantial loss of plasma has taken place, it rmight be preferable if gelatin is dissolved in a physiologic saline solution instead of distilled water. The presence of such a solution assists in restoring ionic balance. A long term treatment with such a gel may not be preferable, in an advanced phase of the healing, when the liquid losses have been compensated, a gel dissolved in distilled water should be used. It can be supposed that in a physiologic environment the regeneration process of the cells slows down probably owing to the lack of any triggering stimulus.

Preferably the gel can also comprise conserving agents.

The gel made according to the invention can be used for treating primarily burns, ulcus cruris and decubitus, however, owing to its general wound healing effect its field of application can be extended to the treatment of other kinds of injuries as well.

Several properties of the gel renders a wide range of prospective applications also in the field of cosmetics. This hypothesis can be based by the excellent penetration properties of the gel into the deeper layers of the skin, thus it can facilitate the metabolism throughout the whole depth. The gelatin based gel can act as a carrier for other active agents, and this property substantially widens its field of use.

According to the invention a method has also been provided for preparing a gel with increased oxygen content, comprising the steps of heating the gel to a temperature slightly above the melting temperature thereof to take a liquid state, introducing oxygen gas into the liquid under an overpressure of at most 6 Mpa in a closed space, mixing the liquid with oxygen, cooling the liquid until gelling, and maintaining the overpressure throughout these steps.

It is preferable if the gel is gelatin.

In a preferable embodiment of the method further active agents and additives like a non-oxidizing antibiotic, boric acid, glucose or conserving agents can be added to the gel prior to the cooling step.

A preferable embodiment of the method comprises the step of feeding the gel when it is still in liquid form into containers with closed space, closing the containers under the initial overpressure, and allowing the liquid to cool down and get gelled in the containers.

The method is simple and it does not require special equipment or technique. The gel should be filled into cans or flasks that can be exposed to the operational pressure. The discharging of the gel from such containers can be solved by means of a driving gas separated preferably from the space comprising the gel. In that case double walled containers should be used, wherein the inner container should have flexible walls to collapse under the pressure of the driving gas between the two containers.

The invention is defined by the accompanying claims.

The invention will now be described in connection with examples and experiments that demonstrate the effects of the gel. The results of the experiments will be illustrated on the basis of the drawings. In the drawing:

Figure 1:
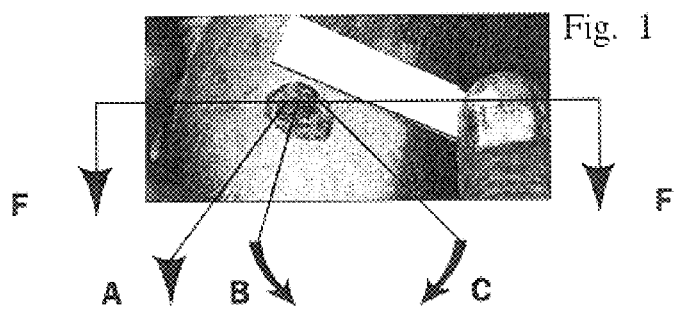
FIG. 1 is a sketch illustrating the different markings used in the microscopic cuts.

EXAMPLE 1.

25 g gelatin alba granulate obtained from a drugstore was soaked in 100 ml distilled water through 3 hours in a thermostat at a temperature of 55–60° C., then with the further addition of distilled water of the same temperature it was diluted until a total volume of 1000 ml was reached. The solution was then filled into a stainless steel cylindrical bottle with a volume of 21 and preheated to the temperature of the solution. A gas inlet duct with a closing valve was provided in the bottle which was connected to an oxygen supply line capable of feeding oxygen at a pressure of 0.5 MPa. Near to one end of the bottle an outlet duct with a closing valve was provided, and the outer end of the duct was designed as a rapid connector made mainly by Teflon so that one end of a disposable syringe could be quickly attached thereto.

After filling the solution into the bottle the valve leading to the oxygen supply was opened, and the inner space was filled with oxygen under a pressure of 0.5 Mpa.

The warm bottle was placed on a rotating mixer which caused slow rotation (5 to 10 rev./min.) of the bottle around an axis normal to its central axis. The bottle was rotated as long as its temperature cooled down to 25–30° C. In about 30 minutes long periods the oxygen supply valve was repeatedly opened, and the bottle was completely filled again to compensate for the gas particles taken up by the liquid. After the bottle was cooled down to room temperature, it was stored in a thermostat adjusted to 16–18° C. This cooler temperature was required, since in the experiments no stabilizer was added to the gelatin.

The so obtained material will be referred to hereinafter as "proloxin" that expresses its oxygen and proline contents. Under operational pressure this material is a transparent gel, while under atmospheric pressure and room temperature the transparency is lost and an opaque gel is obtained. If the gel is fed into a Petri dish, its opaque appearance is maintained through several hours.

When the gel is exposed to atmospheric pressure, a portion of the oxygen comprised in the gel will be released accompanied by a soft sputtering noise. Owing to the high surface tension and low gas release property of the gelatin, the oxygen gas will be encapsulated in the material in the form of tiny bubbles, and the refraction of the light at the boundaries of the bubbles causes the opaque appearance.

We tried to determine the actual oxygen content of the proloxin by means of electrochemical methods (by using the equipment "Chemical Microsensor" made by Diamant General Ltd. U.S. and using Clark miniature electrodes therewith). The measurement showed oxygen content above the upper limit of the measurement range (i.e. higher than 0.2 Mpa), and this value was reached after about 30 minutes following the exposure of the gel to the free atmosphere.

When the gel was warmed up to the temperature of human skin (about 30–32° C.), it slowly melted and oxygen was gradually released. The excess oxygen content was lost after about 1.5–2 hours.

For determining the oxygen content of the gel freshly fed in a syringe, the gel was heated in a closed space to melt, then it was cooled down again, and the partial pressure of the oxygen was determined from the volume of the gas escaped form the gel. As a result 0.49 MPa was obtained which (within the tolerance range of the measurement) was practically the same as the initial pressure in the bottle, thus the gel in the syringe had the same oxygen content as it had in the bottle.

In order to prepare a control material for the proloxin a 2.5% gelatin solution was made with a similar method but without the addition of pressurized oxygen. This control gel was also stored at a temperature of 16–18° C.

EXAMPLE 2

1000 ml gelatin alba solution was made as described in Example 1, and 25 mg from the drug under the trade name Gentamicin (made by Chinoin Pharmaceutical Company, Budapest) was added. The active component of Gentamicin is gentamicin sulfate (Dr. Alföldi, Sándor: Gyógyszerkódex, Budapest, 1992). This concentration corresponds to the dosage suggested by the literature.

Gentamicin was added to the solution just prior to its feeding into the closed space, in any other respect the material was prepared as described in Example 1. The gel with gentamicin has the same physical appearance and properties as the one described in Example 1. The gel with such a gentamicin content will be referred to thereafter as "proloxin G".

For analyzing the effect of the presence of oxygen a control gel without oxygen has been made, wherein 1000 ml contained also 25 mg Gentamicin. This control material will be referred to as "gelatin G".

EXAMPLE 3.

The preparation of the gel described in Example 2 was modified in such a way that together with the addition of gentamicin, glucose was added to the 1000 ml solution in such an amount that the glucose concentration of the whole solution became 34 mM/l.

The preparation method was in all other respect identical with that described in Example 2, the addition of glucose did not change the physical properties of the final product.

The gel that comprises gentamicin and glucose will be referred to as "proloxin G+g".

EXAMPLE 4

The preparation method as described in Example 3 was modified in such a way that instead of using distilled water, a physiologic saline solution was used. In view of the fact that the object of the gel to be prepared was to treat burn wounds of guinea pigs, in the physiological solution a $K^+$ and $Na^+$ serum electrolyte concentration was provided which is measurable in the blood of guinea pigs. The serum electrolyte level of the guinea pigs participating in the experiments was:

$Na^+$: 145 meq/l $K^+$: 4.5 meq/l.

The physical properties of the so obtained gel was not modified by the presence of sodium and potassium ions, and the final product will be referred to as "proloxin G+g+P".

EXAMPLE 5

The preparation of the gel described in Example 2 was modified in such a way that gentamicin was not added and as solvent instead of pure distilled water boric acid of 3% concentration was used as solvent and glucose was added like in Example 3.

As it is well known in the art, boric acid does not irritate the mucous membrane, it can well be stabilized and has bactericidal and fungicidal effects. Such a gel can be applied to healthy skin surfaces or to smaller and shallow skin injuries. The application of boric acid to open wounds is contraindicated. The use of boric acid has been contemplated for cosmetic treatments and for treating smaller skin injuries, wherein the bactericidal and fungicidal effects might be preferable.

The physical properties of the so obtained gel were not affected by the presence of the boric acid, and the final product will be referred to as "proloxin B".

Experiment 1

For demonstrating the effects of proloxin Wistar type male rats of 250–300 g weight were taken. The hair was removed in dorsolateral direction at both sides below the lower rib line. Under narcosis (by means of ketamin) a circular stamp with a diameter of 1 cm heated to a temperature of 205–210° C. was applied for a period of 8 sec on the previously sterilized skin surfaces from where the hair had been removed, whereby burns of third grade (combustio escharotica) were provided.

Three kinds of treatments were applied thereafter:

treatment without any active ingredient, wherein the wounds obtained normal toilet only, i.e. periodic cleaning of the wounds by means of distilled water, and this treatment was used as first control;

treatment with normal gelatin (a 2.5% water based solution of gelatin alba prepared under atmospheric pressure), this was used as second control;

treatment with proloxin made according to Example 1.

For minimizing the effect of individual differences between the animals, a self control was used at each experiment which means that on the same animal the left side wound was treated as a control and the right side wound was treated with proloxin.

The animals were treated twice a day through 7 days in a ketamin narcosis, and the free surface of gelatin was covered by a sprayed layer of Plastubol (a usual wound covering spray). By using a covered treatment the likelihood of spontaneous oxygen release before the full absorption of the gel into the skin was decreased. The healing process was demonstrated by photos taken on the 1st, 7th, 12th and 21st days.

After each treatment when the effect of narcosis ended, in both sides of the animals the wounds and their environments were washed with distilled water and the remains of Plastubol films were removed by acetone. In four days intervals tissue samples were taken by microbiopsy, and the samples were prepared by means of routine nucleus painting technique.

Clinical Experiences Obtained During the Treatment

Treatment with the first control: the scabs peeled off between the 7th and 9th days. At the untreated (control) side the necrotic skin remains peeled off by 1–2 days earlier. The daily two narcosis caused feeding and behavior problems after the first week (starting aphagia, decreased startle reaction) and this justified the termination of the treatment. The agressivity of Wistar rats did not allow the treatment without narcosis.

The healing of the control side was typical, from the demarcation lines of the wounds towards the central regions an even healing process took place, by the 21st day a healed area could be seen with a visible scar without any hair growth.

Treatment with the second control: to determine whether the differences between the treated and control sides were due to the application of gelatin as such or due to the gelatin with the encapsulated oxygen therein, in this group the left side of the animals were treated with normal gelatin and the other side with proloxin.

The observation of the healing process demonstrated a uniform overall healing of the wound area treated by proloxin, while normal gelatin, although substantially facilitated the healing process itself, did not change the conventional character thereof to slowly proceed from the wound edges towards the central area. Hence, the difference lied between the uniform healing of the whole wound surface and the gradual healing directed from the outer zones to the central one. The status obtained by the 21st day demonstrated that the wounds at the left side treated by normal gelatin healed by leaving cicatrices and had a rough touch, while the side treated by proloxin had a smooth and evenly healed surface, and hair started growing on the healed area.

During the experiments neither bacterial nor fungicidal infections were experienced. No allergic skin reaction was triggered by the use of the Plastubol spray either.

Histologic Observations

With regard to the small number of the test animals cuts of 1×2 mm size were taken in four days' periods for histologic examinations both from the treated and control sides. Owing to the small size of the samples we could not correctly position the cuts, therefore our histologic observations are based on the average impression obtained from a large number of samples. The excisions were taken in case of each sample both from the central and edge regions of the wounds.

From the several hundred cuts in almost the full cross section of the wounds under the scabs an increased multiplication of nuclei was observed at the sides treated with proloxin, and the scabs peeled off by 1 or 2 days later than at the control side. Such a multiplication of nuclei was not present in either the cuts taken from the wounds of the control side or in those taken from the side treated by normal gelatin. The results of histologic examinations confirmed the visual observations of the wound healing reported hereinabove.

The histologic examinations did not include the observation of tonofilaments and vascularisation.

Experiment 2 a) The Selection of Experimental Animals

Although the Wistar rats used in Experiment 1 was an albino species bred and selected through several hundreds of generations, our objective was to examine less uniform animals with differing skin types, and to determine the effects of different types of proloxin on the healing of combustio escharotica.

Based on further considerations, e.g. the tracing of the regeneration process of tonofilaments, it seemed preferable to chose experimental animals that similar to humans do not synthesize vitamin C i.e. obtain it by means of nutrition. An important further factor in making this selection was the thickness of the skin of the experimental animals; because by using a species of sufficiently thin skin, the establishment of burns in the range from combustio bullosa to combustio escharotica i.e. up to burns of fourth grade is easier without insulting the adjacent surface areas.

It is known that the immune system of guinea pigs compared to that of Wistar type rats is closer to the human immune system. Based on this fact and on the above considerations, we have chosen guinea pigs as experimental animals. A further reason of this choice was the peaceful nature of guinea pigs owing to which we could carry out daily two treatments without applying narcosis. A further advantage of this species lies in the largely different individual skin types including the range starting from the albino individuals till the fully pigmented ones. The experimental animals were taken from a cavia porcellus (respectively from cavia cobaya) breed, from which 50 males of 250 to 300 g mass were taken. In forming experimental groups from these animals, no selection according to the extent of pigmentation was made.

b) Determination of the Main Parameters of the Experiments

Without having reliable literature sources regarding these animals, we have experimentally determined the plasma electrolyte and blood glucose levels and the required extent of ketamin (Calypsol) dose used for narcosis. The vena femoral of two of the animals was prepared by using a narcosis of 3 ml/kg Calypsol (i.e. 50 mg ketamin in 1 ml distilled water). The value of the serum electrolyte referred to in Example 4 was determined on the basis of blood samples taken from these animals.

The blood glucose level was 9.5 mM/l.

In a pilot experiment the dose of Calypsol narcosis was tested through the steps of 4 ml/kg, 3 ml/kg and 2 ml/kg. Here an animal was lost. Guinea pigs have very small tolerance against such narcotics which proved to be problematic. In determining the above parameters altogether three animals died.

In further two animals the temperature and duration of the experimental burning was tested.

In this way the number of the actually tested animals was 45. They were assigned in three groups referred to as I, II and III, and in each group the animals were designated by capital letters of the alphabet.

c) Description of the Experiments

On the back of the 15 animals in group I in both sides under the arch of the lower ribs, at the height of the kidney the hair was removed along a stripe of about 3 cm width by means of Cooper scissors. The remaining hair was removed by means of a cream. The burning of the designated areas of the narcotized animals was carried out by means of an automated stamp heated to 170–180° C. and applied through 18 seconds as established earlier experimentally during the pilot tests. This caused third to fourth grade burns and was carried out uniformly so that both sides of a pilot animal used as control for the burning step healed identically and in the same time.

Just after the burning and each day thereafter every morning between 8 and 10 a.m. and every afternoon between 5 and 7 p.m. each animal obtained a treatment. In group I. the treated areas were covered by means of locally made circular plasters, each consisting of a cellophane foil and an adhesive stripe, placed by means of a tool on the hairless skin area around the wounds. The cellophane foil was chosen because this material has minimum gas permeability even in wet state.

During this series of experiments the wounds at the right sides were treated with proloxin G as made according to Example 2. The left sides received only a wound toilet. The proloxin G used during the treatments was fed previously into a syringe and was thereafter fed therefrom by means of a motor driven piston under the plaster. A thin drain tube was used to let air out from the space below the plaster.

Unfortunately, the double foiled plaster became loose after getting into contact with gelatin, therefore when gelatin became liquid at the skin temperature, leakage was experienced.

From the 7th day of the treatment of group I. another covering method was used. A surgical rubber finger cot was placed and affixed on the hairless intact skin surface in a wound up state by means of an appropriate tool and by applying a Plastubol wound cover adhesive. This rubber cap was pierced by a needle to provide an air path and the gel was fed by means of a further injection needle. The majority of the experimental animals tolerated the presence of the so applied rubber wound covers through 1–2 hours. Well before the expire of this time the gel was absorbed by the skin, whereafter the caps gradually fell off, probably owing to the hydration of the skin. At a few number of occasions the caps were removed by using a wool-thread immersed previously in acetone. The full absorption of the proloxin G gel required about 25–30 minutes.

After each treatment the skin areas around the wounds were cleaned from the remains of Plastubol by means of acetone. After removal of the wound cover both sides obtained similar wound toilet consisting of the application of a lukewarm pack of distilled water followed by a cleaning also with distilled water.

Although the treatment was a covered one, the daily two therapies of 20–30 minutes each gave together such a short resulting time that the wound healing can be regarded as one without a coverage.

During the treatment, in five days periods, skin samples were taken from randomly selected animals. The samples were about 0,5 cm wide and 2 cm long. The excisions reached till the surface of the fascia. The samples were loosely fixed by means of wooden nails on a carrier member of 10 mm wide and 5 mm thick cut previously from a rubber eraser and provided with a U-shaped cut recess at one side. After providing individual markings on the samples, they were immersed in a 10% formalin solution. These samples were sufficiently large to enable preparation of longitudinal and transverse cuts from the intact, edge and narcotized wound regions, and the cuts were exposed to different kinds of painting methods.

d) Clinical Experiences

The experimental animals did not obtain general treatment or proteolytic drugs or painting with merchurochromat. The combustio escharotica was so large that two animals (I/B and I/H) were lost in an hour following the burning owing to the shock caused by the intervention, and a further animal (I/A) was lost after two days in spite of all efforts.

In two animals (I/N, I/S) ascites was manifested. Excisions were made on the 5th day following the burning on the animals I/j and I/L, on the 10th day on the animal I/C, on the 15th day on the animal I/D and on the 20th day on the animals I/F and I/S. When the experiment was finished on the 20th day, eight animals remained for observation.

As a general experience, the plasters were tolerated in different extent and for differing periods. At the sides treated with proloxin G the scabs peeled off by 1–2 days later than at the other sides.

Pictures were taken from all members of the whole experimental group in every 5th day.

In spite of the short daily treatment, by the 10th to 12th days remarkable differences were observed in the healing of the treated and control sides. On the treated sides of the animals, which tolerated the treatment following the peeling off of the scab, large areas of fresh proliferating tissues were seen which covered the whole wound surface by the 15th day. On the control side the healing proceeded lege artis from the intact areas through the wound edges towards the central regions.

When the untreated wounds were touched by hand, one could well feel that deep ulcerous recesses remained giving a rough touching sensation. The wounds at the treated sides healed faster and already by the 10th–12th day they did not extend till the fascia, and the wounds gave definitely less rough touch or they were not rough at all.

At the treated side the healthy skin surface around the wound area were shaved by a miniature electric machine. This shaving was not carried out at the control side (because it was not needed for positioning the plasters).

The pictures taken on the 5th day might be misleading, because the ongoing peeling off the scabs at the untreated sides showed a worse surface than at the other side. The narcotized areas peeled off later at the treated side. The pictures taken on the 10th day show the wounds after the scabs have peeled off at both sides. It should be noted that in the narcotized areas the natural process of peeling off the scabs was finished artificially by using surgical methods. The pictures taken on the 15th days show large differences between the two sides. The differences between the healing of the two sides are slightly hidden in the pictures taken on the 20th day owing to the daily shaving of the treated sides while the control side healed spontaneously. On the control side the central area still had a deep wound, while the treated side has been healed.

e) Results of the Histologic Examinations

The skin samples collected during the experiments were embedded in paraffin and cut thereafter to slides of 20 micron thickness. From each sample 8 to 10 cuts were made in such a way that the central and edge wound areas were all represented in respective cuts. The cuts were then usually processed including painting with a haematoxin-eozin nucleus paint.

During the examinations the cuts taken from the control and treated sides of the same animal were compared.

FIG. 1 shows the markings used in the subsequent figures. FIG. 1 is a picture taken from a wound, and the cut used for the histologic examinations was taken in the sectional plane F—F. This plane extends through the whole length of the wound. Since the wound can be regarded to be symmetric relative to its center, arrow A designates the wound edges, arrow C designates the central area and arrow B the intermediate regions which lie between the edge and central areas.

Figure 2B:
FIGS. 2a–2c are cuts made from a healthy skin.
Figure 2A:
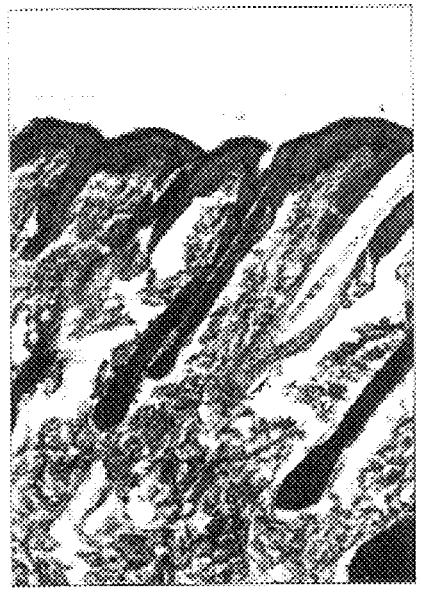

FIG. 2a shows a cut taken from a healthy skin of a guinea pig with a magnification used in the farther figures. The horizontal arrow D designates a further enlargement, thus FIG. 2c is the enlarged picture of the area taken from the starting region of the arrow D (i.e. from FIG. 2a), and in a likewise manner FIG. 2b is an enlarged detail of a portion of FIG. 2a.

Figure 2C:
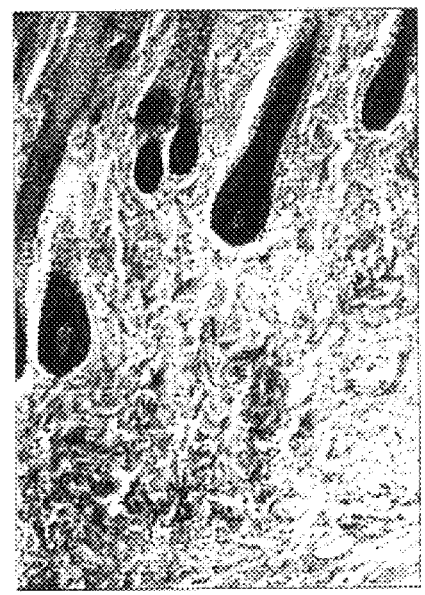

The structure of the healthy skin can well be seen in FIGS. 2a, 2b and 2c.

Figure 3A:
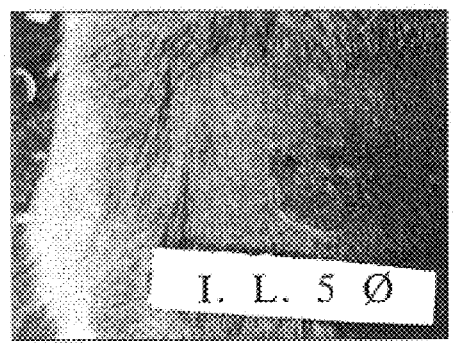
FIGS. 3a–6c are cuts that show the results of experiment 2.
Figure 3B:
Figure 3C:

FIG. 3a shows the untreated left side of the animal L of group I on the 5th day, FIG. 3b is a cut taken from the edge of the wound, and FIG. 3c has been taken from the central portion. Either the number 0 or the letter B in the picture labels always refers to the untreated or left side, while in the labels of the treated side the letters K or J (abbreviation of the Hungarian terms for "treated" or "right") are used.

Figure 4A:
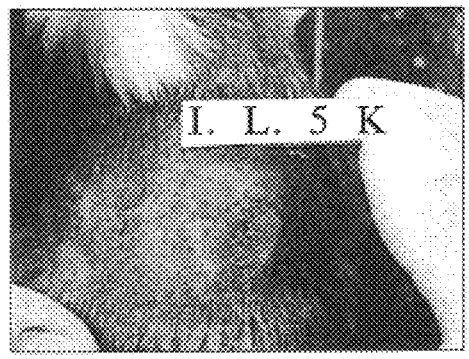
Figure 4B:
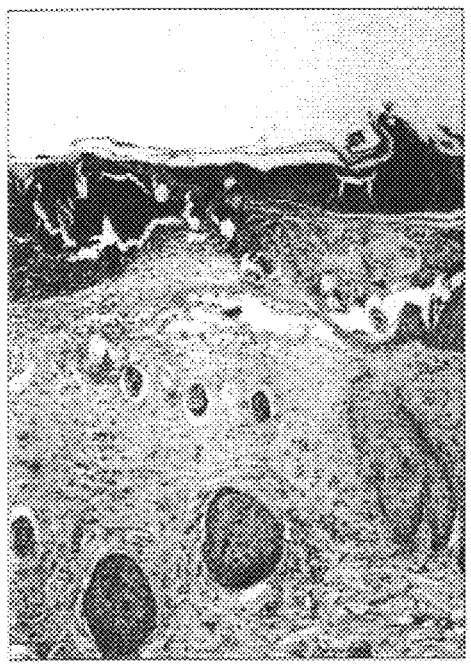
Figure 4C:
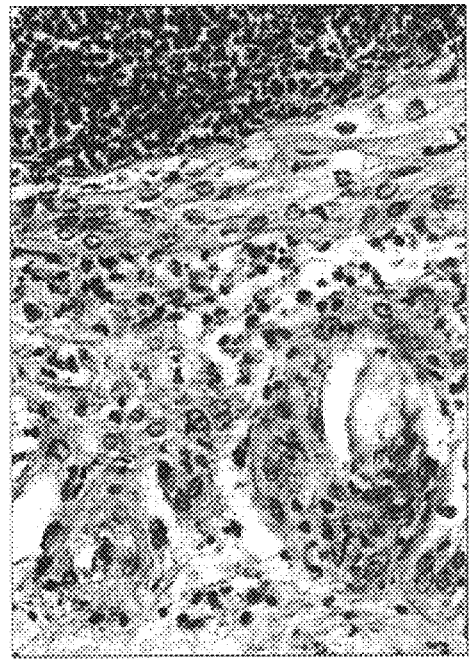

FIG. 4a shows the wound at the treated side of the same animal, FIG. 4b is a cut taken from the central portion of the wound and FIG. 4c is an enlarged detail of this cut.

From the comparison of the two cuts taken from the central wound regions it can be seen that the outer wound regions are both destroyed, at the untreated side deeply below the surface there are no cells visible, and the healing or regeneration process has not yet started. The situation at the treated side is completely different. FIG. 4c shows that the formation of the skin layers has started, this is demonstrated by the visible vacuolums and the formation of capillaries as well as by the visible papillarization. An intensive cellular proliferation can be observed. This all are in contrast with the diffuse regions at the untreated side. From the comparison of the two sides it can also be observed that at the treated side the healing has started from the central area in the deep regions and not from the wound edges. At the untreated side an initial regeneration of the nuclei can be observed in the edge regions, in the central portion, however, there is no regeneration.

Figure 5A:
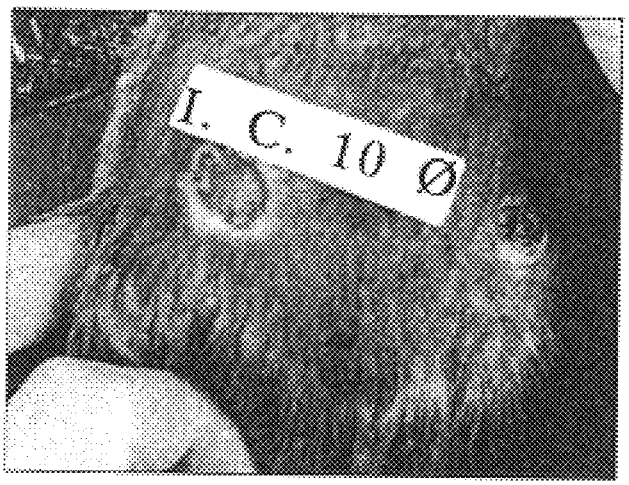
Figure 5B:
Figure 6A:
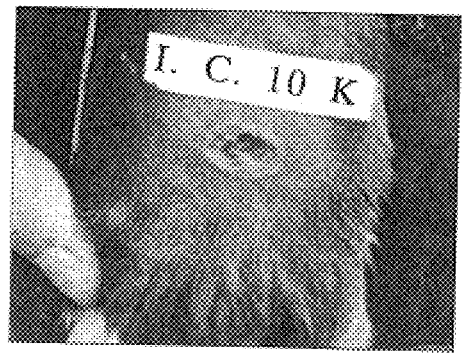
Figure 6B:
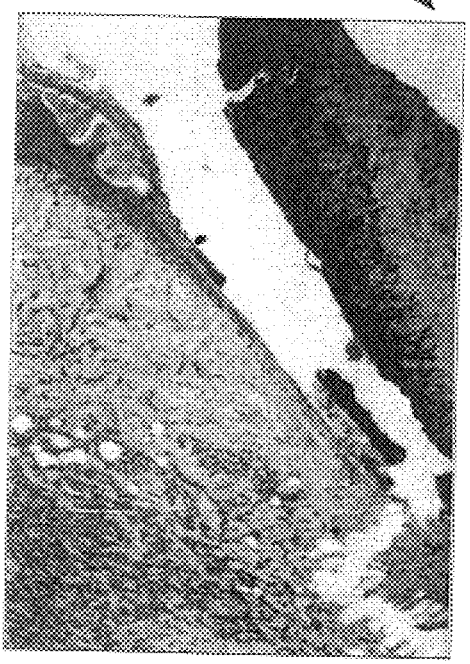
Figure 6C:
Figure 7A:
FIGS. 7a–16c illustrate the results of experiment 3.
Figure 7B:
Figure 7D:
Figure 7C:
Figure 8A:
Figure 8B:
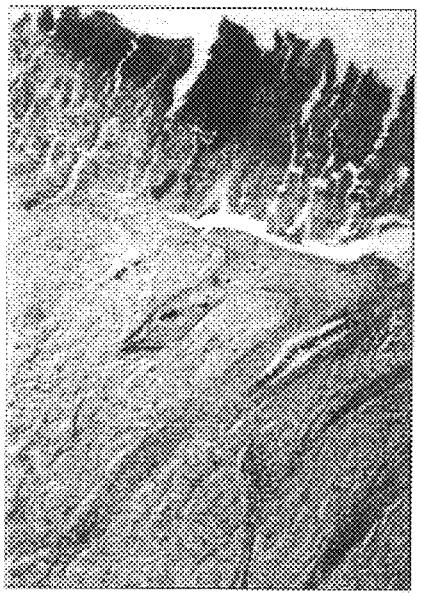
Figure 8C:
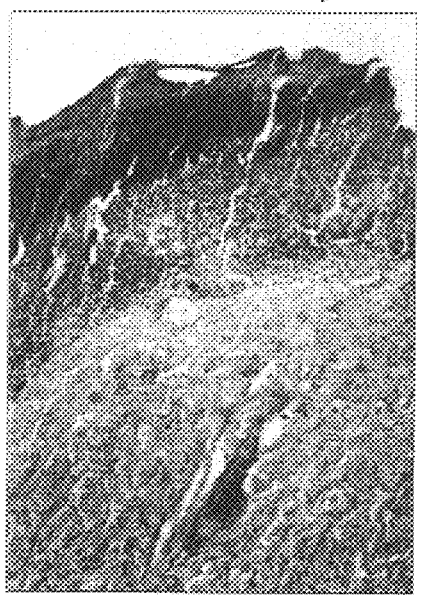
Figure 8D:
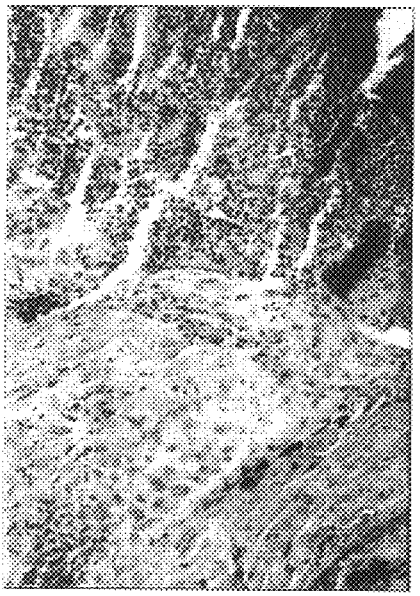
Figure 8E:
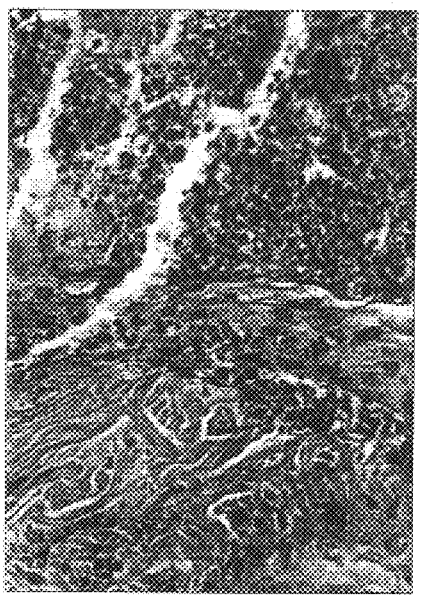

The situation on the 10th day is shown in FIGS. 5 and 6, relating to the two sides of the animal I/C. Here respective cuts are shown from the edge (6b) and central (6c) regions of the treated side.

The formation of a multi-layered structure can be seen also at the untreated side, and the narcotized layer had been peeled off from the surface. At the treated side the peeling off of the narcotized layer has not been completed. At the treated side below the surface a more intensive cell formation can be seen, and the signs of the layered structure of the healthy skin start to appear, while at the untreated side the cellular granulation is less intensive and the layered structure is less developed.

Experiment 3

This set of experiments were carried out on the second group of guinea pigs mentioned in experiment 2. The selection and characteristic parameters of the animals were the same as described in connection with the experiment 2.

There were two differences compared to the previous experiment. The first is the differing temperature and duration of the burning step. The first group was exposed to a burning of comparatively low temperature and long duration. According to our observations this caused ascites in several occasions and the oedema of the adjacent organs. To avoid these effects, in a further pilot test a stamp of 250° C. temperature and burning periods of 2 to 9 seconds were tried to generate serious combustion escharotica. One day after the burning excision was made and that intervention was regarded as a serious third grade burning, wherein the fascia under the subcutane layer was also injured. The corresponding burning time was 4.8 sec and the associated temperature was 250° C. The animals of the second group were exposed at both sides to such an intervention under the circumstances described in the previous experiment.

The second difference lied in the materials used during the treatments of the wounds. The previous experiment can be criticized in that the left side of the animals did not obtain any treatment, while the right sides were treated by proloxin and an antibiotic. The absorption of the proloxin fed under the plaster took place in less than 20 minutes and thereby a therapeutic level of the antibiotic was provided in the blood circulation, the experiment can be criticized on the basis that the improvement experienced at the treated side was due in whole or in part to the antibiotic and not to the presence of oxygen.

During the present experiments the right sides of the animals were treated with the material proloxin G+g as described in Example 3, and the left sides were treated with gelatin G as described in Example 2.

The objective of the present experiment is to differentiate the effects of oxygen and glucose from the combined treatment of the antibiotic and gelatin.

a) Treatment

Both sides of the animals were treated twice a day by using the plaster formed by the rubber finger cot as described in Experiment 2 to cover the burnt areas. At the left side wounds the control materials, while at the right side wounds the experimental materials were injected under the plaster in the way and at the times as described at the previous experiment.

b) Clinical Observations

Based on the observation of the wound healing process it was established that the scabs peeled off at the treated right side without any exception later than at the left side treated by the control material.

The absorption of glucose was determined in Experiment 4, and it was very intensive.

The difference between the treated and control sides was well demonstrated from the excision of the animals II/K and II/P at the 10th day, wherein there was a large injury visible on the fascia at the left side treated by gelatin and gentamicin only, while at the right side the fascia was practically healed. The events in the different deeper layers of the skin like the multiplication of proliferating pluripotent cells or the regeneration of tonofilaments can be seen in the histological cuts only.

The differences in the wound healing were characteristic till about the 15th day. On the 18th day the further treatment of the group was finished. On the 10th day the left side appears to be more healthy which is in accordance with the observation that at the right side the narcotized layers peel off later.

On the 15th day there was a substantial difference between the two sides: in the left side ulcerous areas can be seen, while in the right side the whole wound area seems to be healed. In case of animal II/D there is no visible difference between the left and right sides (owing to the later peeling off the scab perhaps the right side was slightly less healed), but by the 15th day the right side was almost completely healed, and in the left side there was a deep ulcerous area, and in this side the healing process had a progress from the edge regions towards the center area. Similar results were obtained from the other animals participating in this experiment.

If the healing process is compared with the results obtained in Experiment 1, it can be established that the combined effect of proloxin, gentamicin and glucose is more favorable to the healing process than without the addition of glucose. This observation is in accordance with the finding that the glucose and oxygen present in the gelatin under the plaster penetrate by means of a subfusion in the different deeper layers of the skin and will there be utilized in the metabolism. The results obtained in Experiment 2 cannot be attributed primarily to the gelatin and the antibiotic but all components of the material together have a positive effect on the process of wound healing.

c) Results of the Histological Examinations

FIGS. 7a–d show the histological cuts taken from the left wound of the animal II/G on the 5th day and treated by the control material, and FIGS. 8a–e are similar cuts taken from the treated right side. The most significant difference between the two sides is apparent from the comparison of FIGS. 7d and 8c both taken from the central region of the associated wound. The tissues at the control side are diffuse, the density of nuclei is small, while in contrast thereto at the treated side one can observe the newly formed layered structure. The difference between the two sides is substantial also at the edge regions. The regeneration of the skin is well demonstrated in the enlarged pictures of FIGS. 8d and 8e. We can see the already started papillarization, a high density of regenerated nuclei and the formation of collagen fibers.

At the control side the process of peeling off of the narcotized tissues has already started, in the central region it has been completed, while the outer surface of the treated side is still covered with narcotized tissues. From this reason the mere observation of the wounds can be misleading in determining the status of the healing process, the control side gives a better visual impression, although the histological pictures demonstrate that at the treated side the healing process has started from below and has reached a progressive status.

Figure 9A:
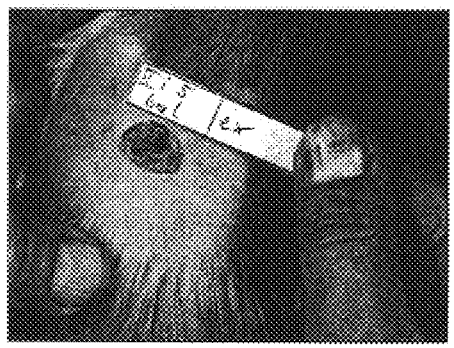
Figure 9B:
Figure 9C:
Figure 10A:
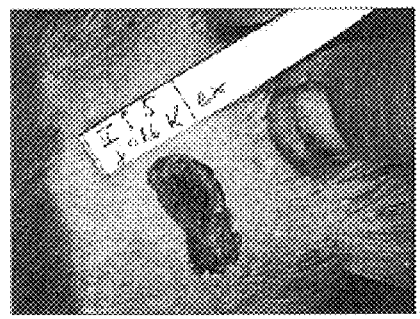
Figure 10B:
Figure 10C:
Figure 10D:
Figure 11A:
Figure 11B:
Figure 11C:
Figure 11E:
Figure 11D:
Figure 12A:
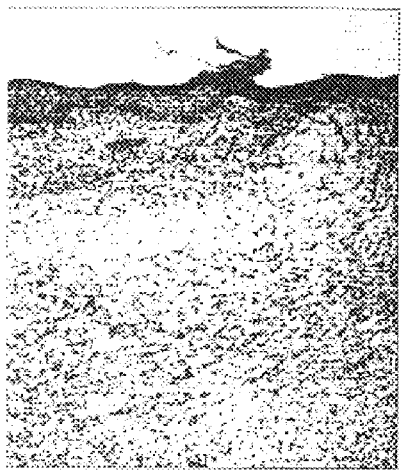
Figure 12:
Figure 12C:
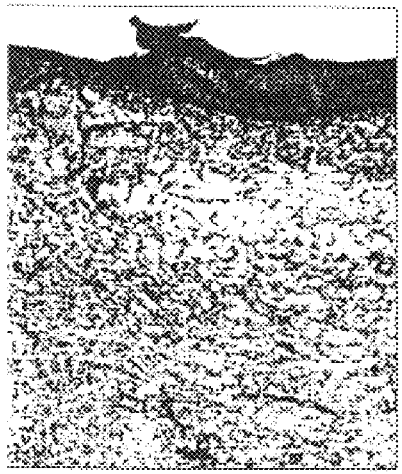
Figure 12D:
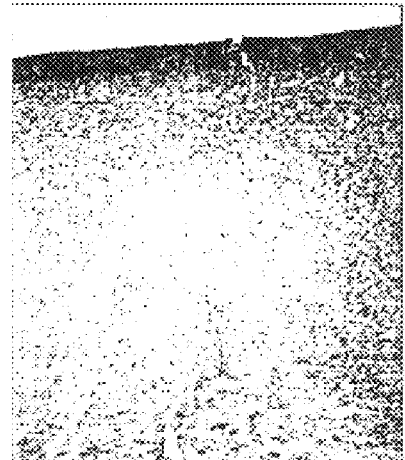
Figure 12E:
Figure 12F:
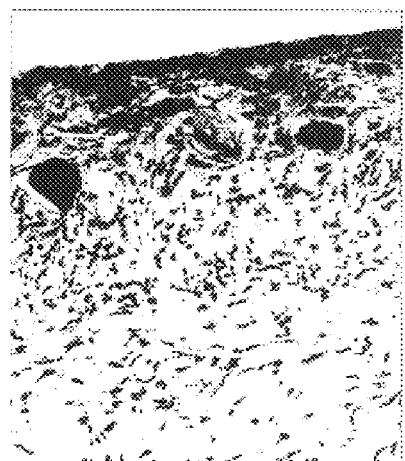
Figure 13A:
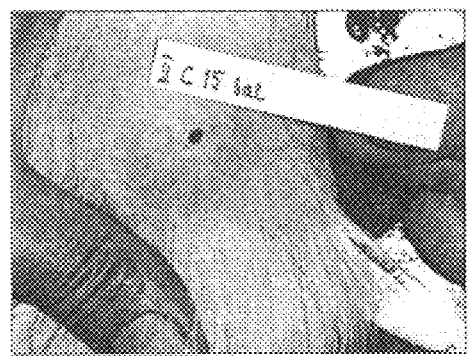
Figure 13B:
Figure 13C:
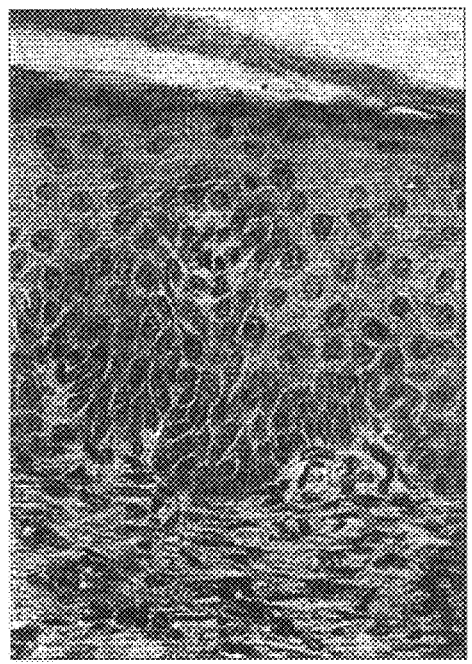

A further pair of cuts can be seen in FIGS. 9a–c (control) and FIGS. 10a–d (treated) taken on the 5th day from animal II/i. The healing of this animal is more advanced compared to the previous one and the differences between the two sides are more apparent. In the cut taken from the edge of the control side (FIG. 9b) a cell proliferation characteristic to the healing at the edges can be seen. The cut taken from the central region (FIG. 9c) shows a much smaller density of cells, and the lower region is still diffuse. The cuts taken from the treated side show high density of cells, well-structured layers and the advanced healing of the central region. The range of white spots at the lower part of both sides show the depth of penetration of gelatin. The combined effect of oxygen, gelatin and glucose resulted in the tissue regeneration can be seen in the treated side, which proves the existence of an appropriate metabolism. At the control side gelatin alone cannot provide any similar effect.

FIGS. 11a–e and 12a–f show cuts taken from the animal II/Z on the 10th day of the treatment from the control and treated sides.

The differences between the two sides have similar character as before, but they relate to a more advanced state of the healing process. At the wound edge regions of the control side the density of cells is quite sufficient, but it is less structured than the tissues in the edge regions of the treated side. At the control side, in the central region the tissues are still diffuse with minimum number of regenerated cells and without any noticeable structure. At the treated side an intensive proliferation of cells can be seen in the whole depth of the wound, and the presence of a suitable layered structure can be observed. The enlarged pictures taken from the edge and central regions (FIGS. 12e and 12f) show the formation of capillaries, and it can be seen that the layers of the cells extend parallel to the skin surface. These pictures are already very close to the ones taken from a healthy skin.

Figure 14A:
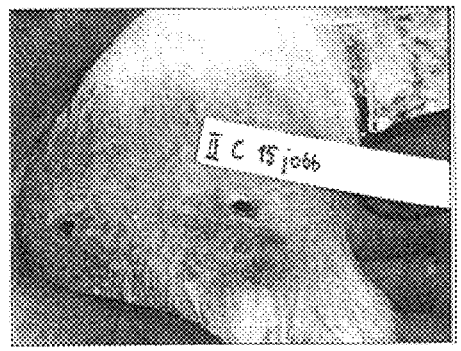
Figure 14B:
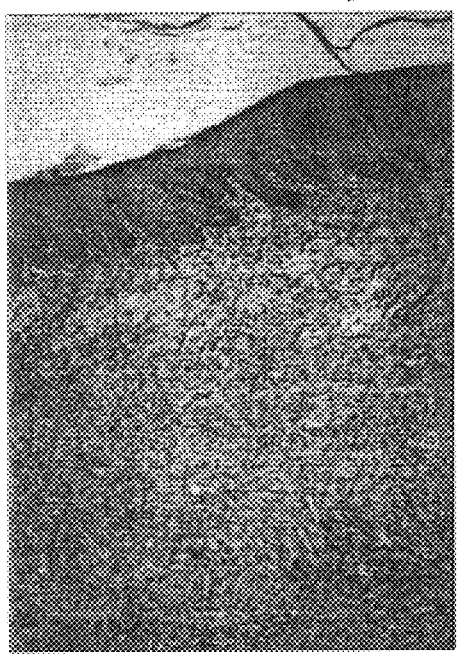
Figure 14C:
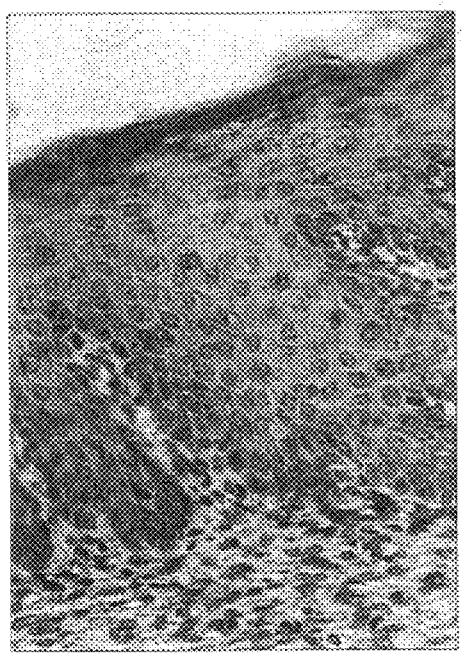

Cuts taken on the 15th day of the treatment from the control and treated sides of the animal II/C are shown in FIGS. 13a–c and 14a–c. At the control side a substantial improvement can be seen compared to the previous FIG. 11, and the enlarged picture shows the initial formation of the basal membrane. The density of cells and of the capillaries is still insufficient. At the treated side FIG. 14b is similar to the picture shown in FIG. 2b taken from the healthy skin, if the differences in the magnification are disregarded. In the enlarged picture the well formed basal membrane and a suitable density of cells can be seen, and the presence of tonofilaments is also normal.

Figure 15A:
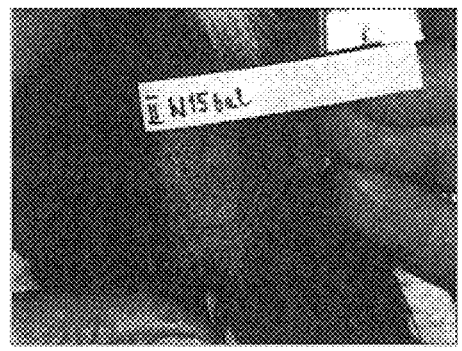
Figure 15B:
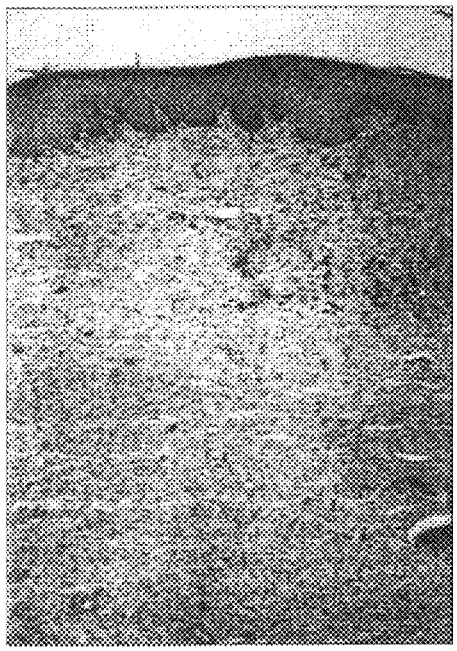
Figure 15C:
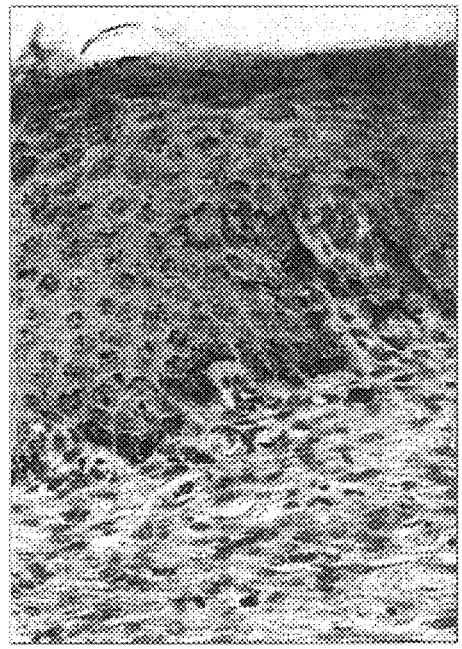
Figure 16A:
Figure 16B:
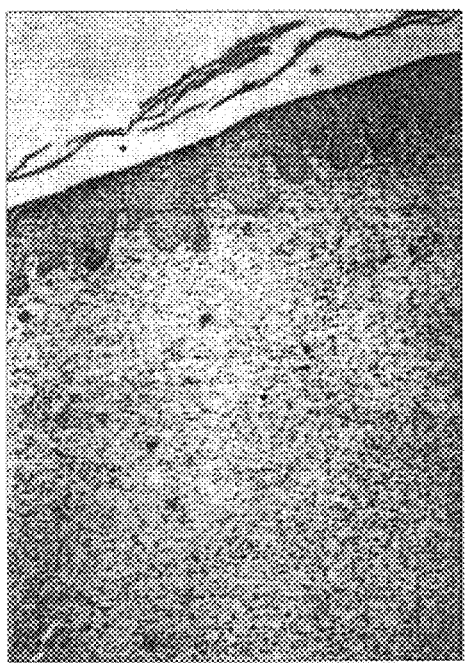
Figure 16C:
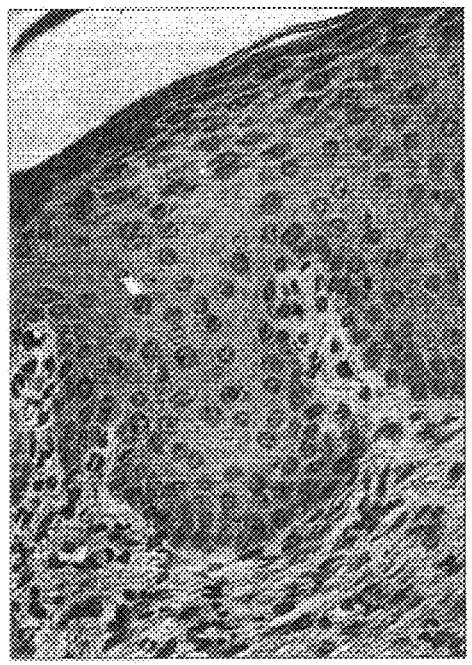
Figure 17A:
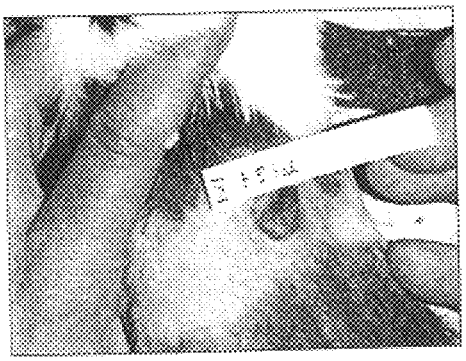
FIGS. 17a–22c illustrate the results of experiment 4.
Figure 17B:
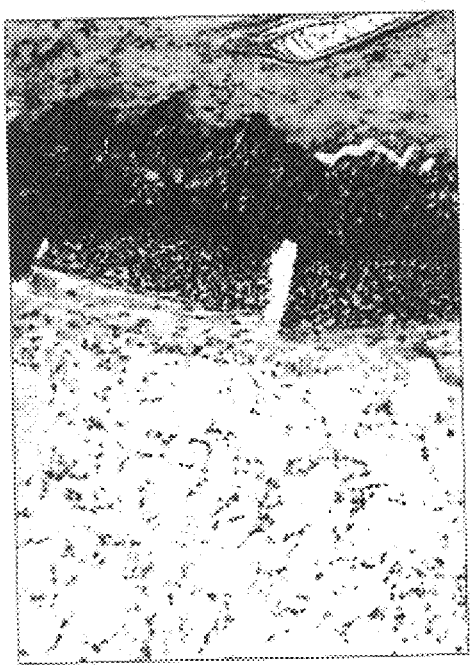
Figure 17C:
Figure 18A:
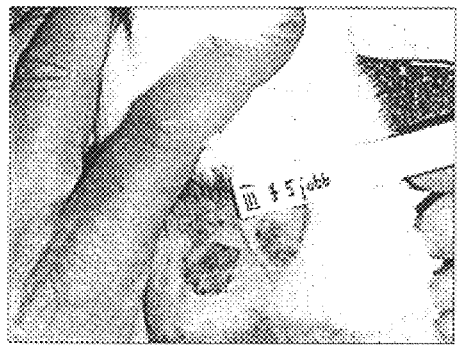
Figure 18B:
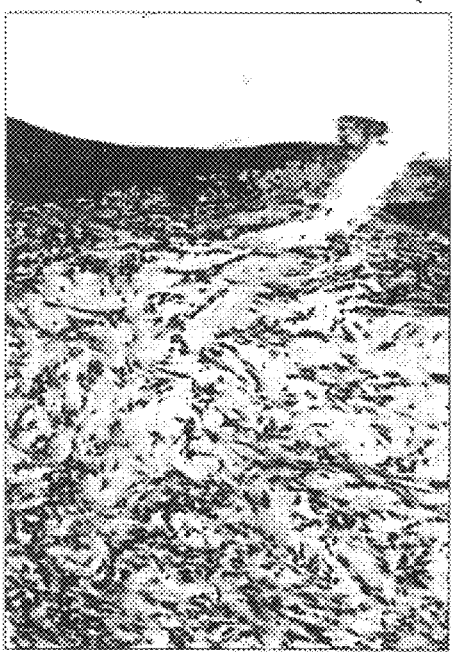
Figure 18C:
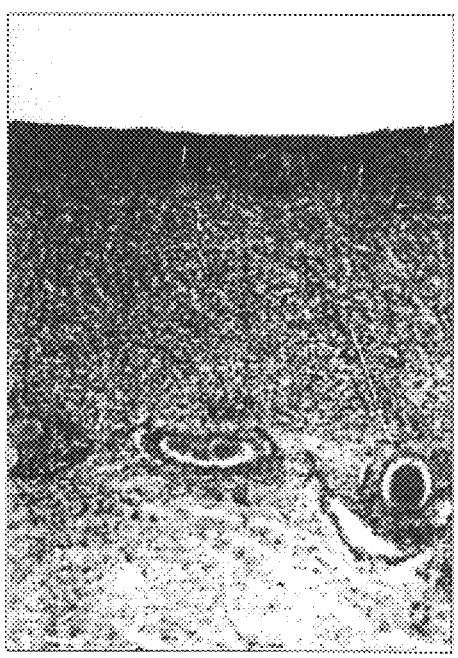
Figure 19A:
Figure 19C:
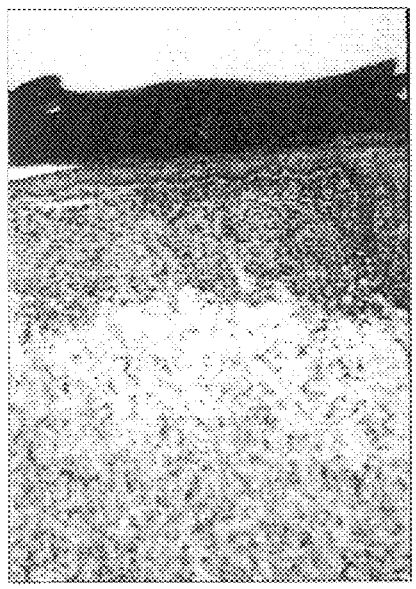
Figure 19B:
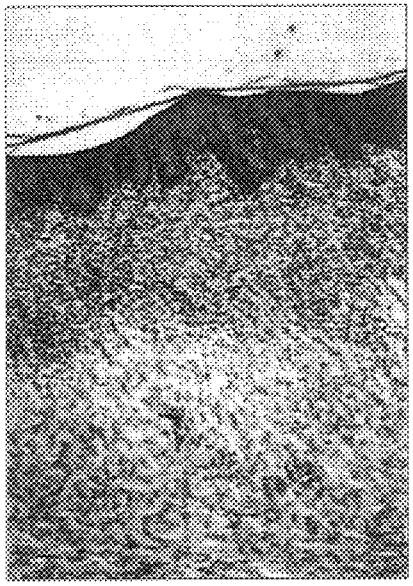
Figure 19D:
Figure 19E:
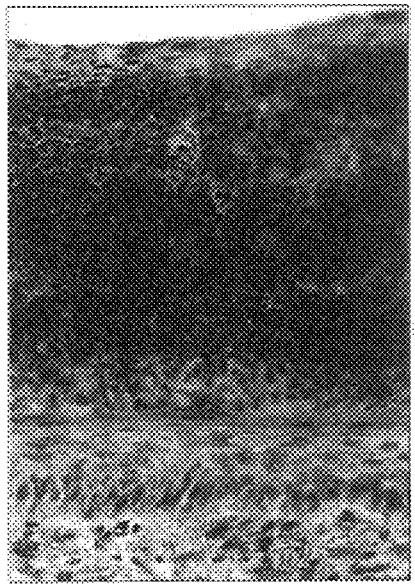

Similar pictures taken from the animal II/N are shown in FIGS. 15a–c and 16a–c. The pictures 15b and 16b made with smaller magnification do not show differences between the control and treated sides, but the enlarged pictures 15c and 16c do. In FIG. 15c taken from the control side, the boundaries of the basal membrane are not sharp and irregular, and the density and form of the cells are also not quite regular. In contrast thereto FIG. 16c taken from the treated side shows a healthy basal membrane and regular cell distribution. The flexible fibers that can be seen in FIG. 16c are missing from the control side. The flexibility of the skin is determined mainly by the presence of these fibers.

Experiment 4 a) Preliminary Considerations

This experiment was carried to determine whether glucose is actually consumed by the skin tissues.

We have supposed that during the absorption of proloxin the oxygen supply alone does not support the process of creating new tissues to a sufficient extent, if the material does not comprise glucose in an amount needed for oxidative metabolism according to the Szentgyörgyi-Krebs cycle theorem. The increased oxygen supply, if this will be used up for the metabolism and if the metabolism follows the Szentgyörgyi-Krebs cycle, requires an increased supply of glucose as well. Therefore, in the experimental material described in Example 3 in addition to the gelatin, oxygen and to the antibiotic, which latter has no role in the metabolic process, glucose has also been added. The Szentgyörgyi-Krebs cycle requires vitamin C as well. In view of the fact that the experimental animals were fed with fresh vegetables, they must have had sufficient supply of vitamin C.

The partial oxygen pressure of arterial and venous blood is known (Klinikai laboratoriumi leletek értékelése—The Evaluation of Clinical Laboratory Results-IV. Edition, Medicina, Budapest 1978, p. 41). The glucose consumption was calculated from human blood glucose data, but it has also been taken into account that the selected animal species has a higher venous glucose level than humans have.

The measured venous blood glucose level of guinea pigs was 9.5 mM/l. The increase of oxygen tension in proloxin (if the arterial oxygen tension of about 13,33 kPa is deducted from the partial oxygen pressure of 0.5 MPa) is about 0,494 Mpa. The partial oxygen pressure difference between arterial and venous blood is about 6 KPa (human data). The relative oxygen pressure increase was therefore 82.2 times.

The difference in the glucose level between arterial and venous blood is 0.22–0.3 mM/l (human data from: Az Élettan Tankönyve—Textbook of Physiology-, Medicina, Budapest, 1965. p. 653). The relative glucose content will be: 9.5 mM/l+(82.2×0.29 mM/l)=34 mM/l, and according to Example 3 this amount of glucose was added to the proloxin.

The question lies now in whether the glucose added to the material proloxin+G will be actually metabolized or not. The objective of the present Experiment 4 is to give a response to this question.

b) Description of the Experiment

In the II. group of Experiment 3 in case of two randomly selected animals on the 5th and 10th days of the treatment 20 minutes following the morning supply of proloxin below the plaster, samples were taken from the gel remained under the plaster and the concentration of glucose remained in the samples was measured. This measured concentration was 6.5 mM/l, thus the initial concentration of 34 mM/l decreased to this value. This fact unmistakably demonstrates that glucose has actually been absorbed in the tissues, and to an extent somewhat higher than the level of our preliminary expectations.

Experiment 5 a) Description of the Experiment

This experiment was carried out on the third group of the experimental animals described in connection with Experiment 2, and with the exception of the materials used for the treatment, the parameters were the same as in case of Experiment 3. The left or control side wounds were treated by gelatin G as described in Example 2, the right side wounds were treated with proloxin G+g+P as described in Example 4.

The objective of this examination series was to determine whether in the serious third-grade burns the loss of plasma during different phases of the healing process can be compensated by the addition of an isotonic physiologic solution.

If the artificial nutrification also requires an anorganic ion supply, then according to our hypothesis the proloxin made from a physiologic solution will speed up the wound healing process. If the artificial addition of plasma is superfluous or disturbing, then there will be no difference or even a negative difference compared to the previous results.

It has been assumed that in case of such small wound areas and of burns of third grade, the addition of an isotonic physiologic solution alone cannot provide surprising results. But bearing in mind that the proloxin treatment can be used to skin injuries caused by other similar mechanisms (e.g. to treating ulcus cruris and decubitus), it appeared logical to try the effect of proloxin made from a physiologic solution when there is a small loss of plasma.

b) Clinical Observations

Regarding the process of the peeling off the scabs there was no significant difference between the healing of the two sides. From the clinical observations it was established that the proloxin made from physiologic solution instead of promoting rather slows down the healing process.

At the end of the experiment, on the 20th day there was no significant difference between the two sides, the healing took place with similar speed.

c) Histological Observations

FIGS. 17a–c and 18a–c are cuts taken for the animal III/J on the 5th day of the treatment from the control and treated sides, respectively. A part of the cuts taken from the edge region shows the unimpaired skin surface, the boundary of the burning is indicated by the white vertical area.

The control side healed quite well, although the density of cells in the central area is small. By that time the narcotized area had not been peeled off, and this and the oblique arrangement of the cut is slightly disturbing. On the treated side the density of cells is sufficiently high both in the edge and central regions, and the formation of hairpin capillaries can be seen in the papilla. The histological picture of the treated side is much more favorable than that of the control side.

Figure 20:
Figure 20A:
Figure 20D:
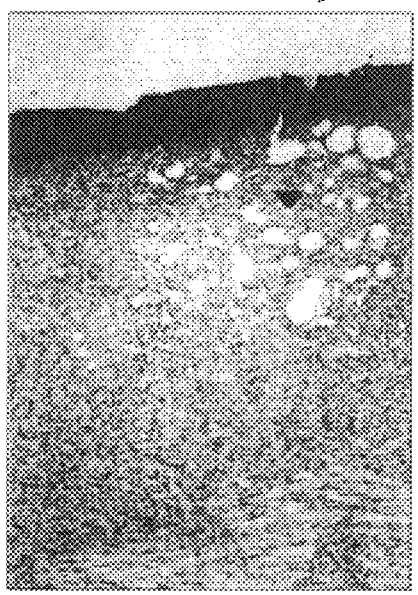
Figure 20B:
Figure 20C:
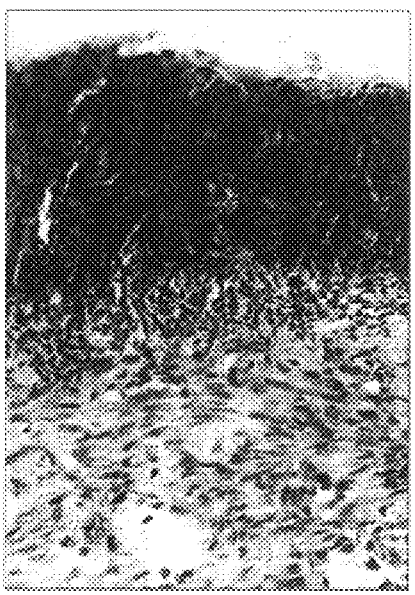
Figure 21A:
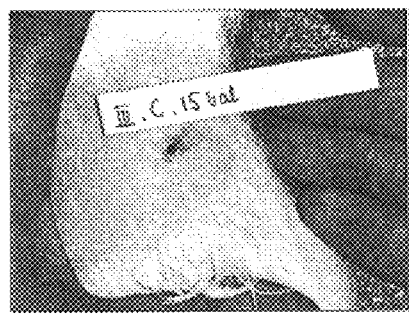
Figure 21B:
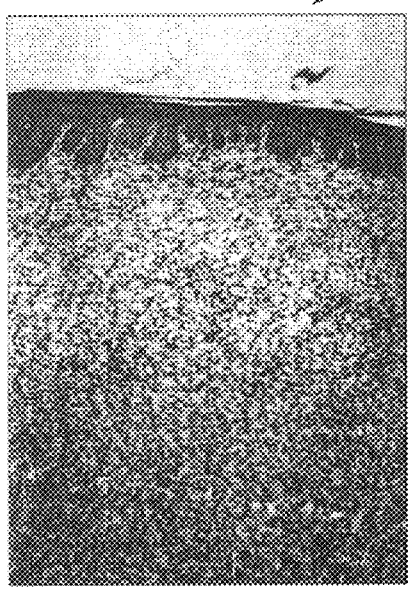
Figure 21D:
Figure 21C:
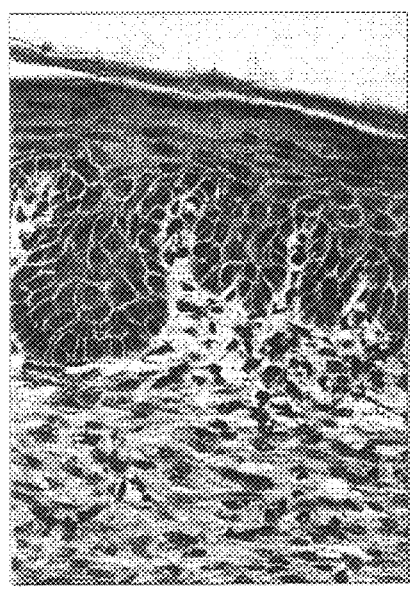
Figure 22A:
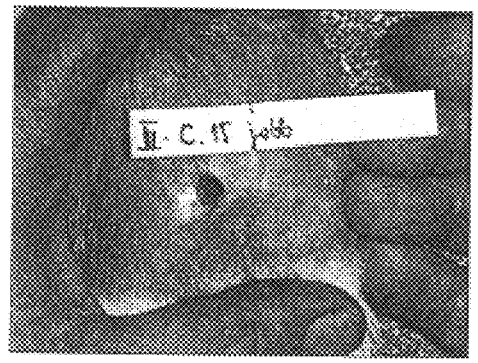
Figure 22B:
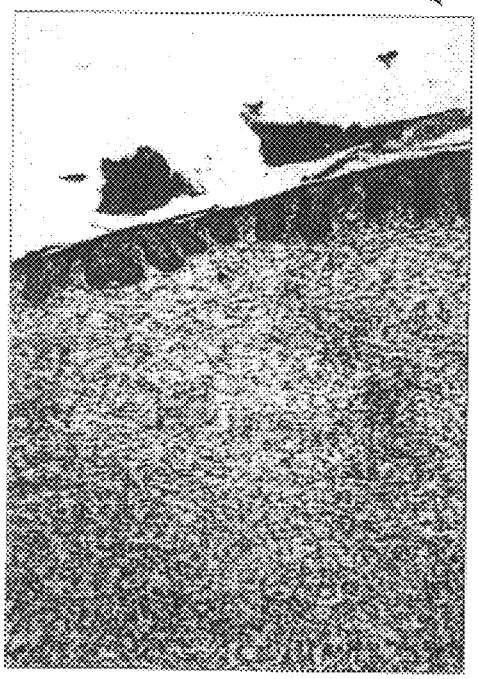
Figure 22C:
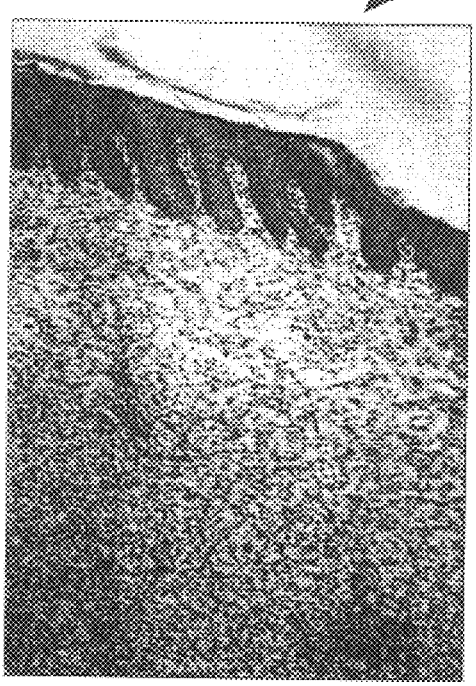

FIGS. 19a–e and 20a–d are cuts taken for the animal III/A on the 10th day of the treatment from the control and treated sides, respectively. From the histological pictures interesting conclusions can be drawn: the order has been reversed, the control side was more favorable than the treated one. In the control side a sufficient cell density and structure can be seen (in case of this animal the natural healing was very good), in the treated side the density of cells was high but the formation of the structure was missing. In FIG. 20c made with the highest enlargement a random cell distribution can be seen without any sign of the formation of the basal membrane.

FIGS. 21a–d and 22a–c are cuts taken for the animal III/C on the 15th day of the treatment from the control and treated sides, respectively.

The histological pictures of the treated and control sides are similar, in both sides a healed structure can be seen.

d) Evaluation of the Observations

The clinical and histological results do conform with each other demonstrating that in case of a treatment with the gel comprising physiological solution the healing process of the treated side is not better than that of the control side.

If the process is observed more closely, this is not the real situation. In case of burnt wounds the loss of plasma is most significant at the time of the injury, and when the scab has been formed, there will be no further loss of plasma at all. At the beginning of the treatment the use of the gel that comprises physiologic solution is justified, and this is reflected by the histological pictures taken on the 5th day.

When the scab has been formed, the presence of a physiologic solution might disturb the natural healing process both in the upper and deeper layers, and with the lack of a natural gradient in the ionic concentration directed from inside to the outside, the natural structure will not be formed. With simple expressions one can state that in a physiologic environment "the cells feel well and there is no need for any change".

In view of such a consideration a treatment seems to be optimum, wherein in the period of intensive loss of plasma (a few days following the injury) the loss of plasma is compensated by using the proloxin that comprises the physiologic solution as described in Example 4, whereafter the appropriate material will be the proloxin G+g according to Example 3.

In case of symptoms with substantial loss of plasma (e.g. ulcus cruris or decubitus) the use of proloxin with physiological solution can be recommended until the healing process is visibly started.

Experiment 6

An accidental event offered a chance for examining the wound healing effect of proloxin B described in Example 5. A man N.G. aged 39 suffered an accident in October 1994 and the outermost finger joints of two fingers on his left hand were amputated. In January 1995 one of the amputated but otherwise healed fingers suffered a further accident at home. He continued working with heavy sheet metals, and in spite of usual surgical treatment his wound did not heal.

Figure 23:
FIGS. 23 and 24 are photos illustrating the result of experiment 6.
Figure 24:

He received a treatment with proloxin B twice a day in each morning and evening so that 3 cubic cm gel was fed under a surgical rubber finger cot. FIG. 23 shows the status prior to the treatment, and FIG. 24 shows the same finger following four days of treatment with Proloxin B. A few days later the wound completely healed.

Three volunteer men of the colleagues of N.G. who suffered injuries from sharp metal sheets which cut the fascia were treated by proloxin B twice a day. The gel was applied under a protective cover. The wounds healed rapidly without any infection, they were not sewed together and Michel straps were also not used.

Experiment 7

Figure 25:
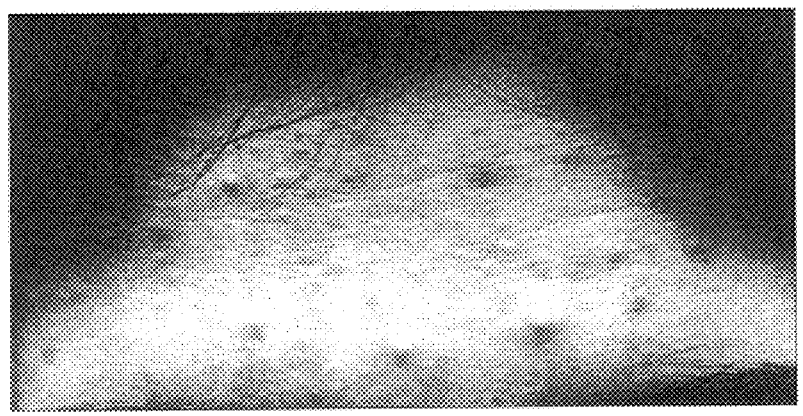
FIGS. 25 and 26 are photos illustrating the result of experiment 7.

For establishing the applicability of the gel proloxin B described in Example 5, the face of a women D.E. aged 24 was treated. Prior to the treatment the patient had had conventional cosmetic care, however, her face and forehead were full with large areas of acne vulgaris. FIG. 25 shows her forehead before the treatment.

Figure 26:
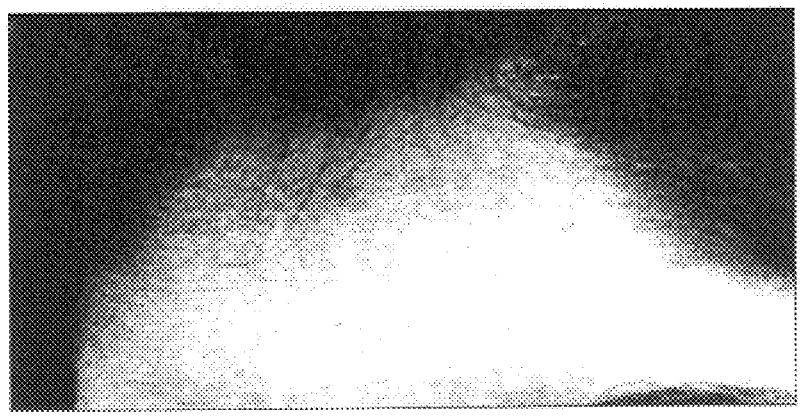

The proloxin B treatment was applied by her cosmetician. The treated area was previously cleaned, then the gel was rubbed in the skin until its full absorption. The treatment was carried out twice a week. Even after the first week a substantial improvement was found, the picture from the forehead area of FIG. 26 was taken at the end of the second week after the fourth treatment. The acne vulgaris disappeared, the skin surface healed. By the end of the fourth week the treatment was completed, and since that time the status of the patient has been good.

What is claimed is:

1. Method for preparing a gelatin for pharmaceutical, cosmetic and/or veterinary use, comprising the steps of:

heating said gelatin to above its melting temperature until said gelatin is a liquid, said temperature being above normal body temperature;

introducing, in a closed vessel, oxygen gas into the liquid so that the pressure in the vessel is at least about 0.15 MPa;

mixing said liquid with oxygen;

cooling said liquid to at least room temperature to enable a gelatin to form having excess oxygen therein in the form of microscopic bubbles; and adding said gelatin to a container, wherein said pressure of the gelatin is maintained above atmospheric pressure during storage in said container, wherein said gelatin further contains a solvent.

2. The method of claim 1, further comprising the step of adding a non-oxidizing bactericide and/or fungicide agent before the end of said mixing step.

3. The method of claim 1, further comprising the step of adding glucose before the end of said mixing step.

4. The method of claim 2, further comprising the step of adding a conserving agent before the end of said mixing step.

5. The method of claim 1, wherein oxygen is introduced into the liquid so that the pressure in the vessel is in the range of from 0.15 to 6.0 MPa.

6. A gelatin for pharmaceutical, cosmetic and/or veterinary use made by the method of claim 1, said gelatin containing excess oxygen therein in the form of microscopic bubbles, said gelatin having an opaque appearance, compared to a clear transparent appearance for the same gelatin without said microscopic oxygen bubbles, said gelatin being maintained in a container and under a pressure of greater than atmospheric pressure until immediately before use, after being released from said container and exposed to atmospheric pressure, said gelatin being able to retain a substantial amount of excess oxygen as a result of the surface tension of said gelatin for a first period of time (T1), wherein said gelatin is able to penetrate into deep layers of the skin or other tissues when applied to said skin or other tissues, and wherein said first period of time (T1) is the same or longer then the time needed for said gelatin to be absorbed by said skin or other tissues (T2).

7. The gelatin as claimed in claim 6, further comprising at the outer surface of said gelatin a covering layer which is applied to said skin or other tissue, wherein said covering layer increases said first period of time (T1).

8. The gelatin as claimed in claim 6, wherein said solvent being distilled water.

9. The gelatin as claimed in claim 6, wherein said solvent being a physiologic saline solution.

10. The gelatin as claimed in claim 6, comprising bactericide and/or fungicide agents.

11. The gelatin as claimed in claim 10, wherein said agent being a non-oxidizing antibiotic applied in a therapeutically effective concentration.

12. The gelatin as claimed in claim 11, wherein said antibiotic is gentamicin sulfate present in an amount of 0.01 to 0.03 thousandth relative to the full gel mass.

13. The gelatin as claimed in claim 11, wherein said agent being boric acid in a concentration of at most 3 mass %.

14. The gelatin as claimed in claim 6, comprising glucose.

15. The gelatin as claimed in claim 14, wherein the concentration of glucose corresponds to the physiological concentration thereof in blood.

16. The gelatin as claimed in claim 14, wherein the amount of glucose is between 10 and 50 mM/l.

17. The gelatin as claimed in claim 6, wherein the pressure of oxygen in the gel lies between 0.15 and 0.6 MPa.

18. Method for preparing a gelatin for pharmaceutical, cosmetic and/or veterinary use, comprising the steps of:

heating said gelatin to above its melting temperature until said gelatin is a liquid, said temperature being above normal body temperature;

introducing, in a closed vessel, oxygen gas into the liquid so that the pressure in the vessel is at least about 0.15 MPa;

mixing said liquid with oxygen;

adding said liquid to a container; and cooling said liquid to at least room temperature to enable a gelatin to form having excess oxygen therein in the form of microscopic bubbles, wherein said pressure of the gelatin is maintained above atmospheric pressure during storage in said container.

\* \* \* \* \*

UNITED STATES PATENT AND TRADEMARK OFFICE
CERTIFICATE OF CORRECTION

PATENT NO.: 6,139,876

DATED: October 31, 2000

INVENTOR: Péter Kolta

It is certified that an error appears in the above-identified patent and that said Letters Patent is hereby corrected as shown below:

On the Title Page, Item 57, in the Abstract, line 8, "ton atmospheric" should read --to an atmospheric--.

In claim 6, col. 17, lines 39-40, "longer then" should read --longer than--.

Signed and Sealed this

Fifteenth Day of May, 2001

*Attest:*

NICHOLAS P. GODICI

*Attesting Officer*   Acting Director of the United States Patent and Trademark Office